US00PP14784P2

(12) United States Plant Patent
Sherman

(10) Patent No.: US PP14,784 P2
(45) Date of Patent: May 18, 2004

(54) PEACH TREE NAMED 'UFBEAUTY'

(50) Latin Name: *Prunus persica*
Varietal Denomination: UFBeauty

(75) Inventor: Wayne B. Sherman, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 109 days.

(21) Appl. No.: 10/306,390

(22) Filed: Nov. 29, 2002

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Susan B. McCormick

(57) ABSTRACT

'UFBeauty' is a new and distinct variety of peach tree which has a winter chilling requirement ofapproximately 200 chill units (cu). The tree is large size, highly vigorous with a semi-spreading growth habit, and bears showy pink flowers. Glands are small and reniform in shape and isolated to the basal portions of leaves. Trees of 'UFBeauty' bear heavy annual crops of early mid-season fruit which are medium large for its ripening season. Fruit have firm, yellow, non-melting flesh which is clingstone. Fruit are uniform, attractive, substantially symmetrical shape, and have an attractive 90 to 100% red skin with darker red stripes. The fruit ripens 3 to 4 days after the beginning of 'UFGold' in early May at Gainesville, Fla.

1 Drawing Sheet

Botanical classification: *Prunus persica.*

BACKGROUND OF THE NEW VARIETY

The present invention relates to a new and distinct variety of peach (*Prunus persica* (L.) Batsch) tree which is named 'UFBeauty' and, more particularly to a peach tree which produces near full red skin, good eating quality, clingstone, non-melting and yellow flesh fruit which are mature for fresh market in early May at Gainesville, Fla. and which are produced on a tree adapted to a mild winter climate. Contrast is made to 'UFGold' (U.S. Plant Pat. No. 10,315) peach tree, a standard variety, for reliable description. This new variety is a promising candidate for commercial success in that it retains fruit firmness at the full flavor, tree ripe stage for 10 days on the tree.

ORIGIN OF THE VARIETY

This peach tree (genotype) originated in a cultivated area of the fruit breeding program at the University of Florida, located at Gainesville, Fla. The seed parent was 'Fla. 90-50CN' (unpatented), a non-melting flesh nectarine [originated as an F2 of (Fla. 84-18C×Fla. 9-20C)] (both unpatented peaches of complex origin). The pollen parent was 'UFGold'. UFBeauty was determined to have unique tree and fruit characteristics making it worthy for commercial fresh fruit production. 'UFBeauty' differs from its pollen parent by having full red skin and has larger size fruit that are produced on a tree less spreading. 'UFBeauty' peach tree was selected in 1998 and was designated and tested as Fla. 98-1C. It was asexually reproduced by budding on 'Flordaguard' (unpatented) seedling rootstock at Gainesville, Fla. where the selection was made and trees were also tested. There are no known effects of this rootstock on this scion cultivar. Asexually propagated plants remain true to the original tree as all characteristics of the tree and the fruit were tranmitted.

SUMMARY OF THE VARIETY

'UFBeauty' peach tree is a new and distinct variety that bears yellow, non-melting flesh fruit, and has a low chilling dormancy requirement. It blooms with 'UFGold' peach tree at Gainesville, bearing a high percentage of red skin. The estimated chilling requirement is 200 chill units, the same as 'UFGold'.

The present invention resulting in 'UFBeauty' peach tree is characterized by fruit of excellent flavor and eating quality. The trees are vigorous, productive and without alternate bearing. Trees attain in two years, a height of three meters and a spread of two meters at Gainesville. Terminal growth of up to a meter annually is common on mature 4-year-old trees with normal pruning to a vase shape. The first fruit ripen in early May at Gainesville or in about 80 to 85 days from full bloom, which is about 3 to 4 days after the beginning of 'UFGold'. The fruit are uniformly large for an early season peach. Ripe fruit have near full(with darker stripes) red skin with small flecks of red pigment throughout the flesh on the sun exposed side of the fruit, especially on trees stressed during hot, dry weather. There is no red pigment in the flesh at the pit. The flower anthers are light red to yellow, a common characteristic of many standard peach and nectarine varieties.

DESCRIPTION OF THE DRAWINGS

The accompanying drawing is a color photograph which shows a typical specimen of the fruit, leaf, and stem of the new variety as nearly true as it is reasonably possible to make in a color illustration of this type.

The photograph shows an attractive shape and exterior coloration of six specimens of fruit above a ruler in a stem end view, a blossom end view, side views facing and perpendicular to the suture, and fruit cut longitudinally showing the flesh with and without a clingstone pit in place.

DETAILED BOTANICAL DESCRIPTION

The tree, flowers, and fruit may vary in slight detail due to variations in soil type, cultural practices, and climatic condition. The potential for commercial production of fresh fruit by 'UFBeauty' peach tree is high, due to its attractive red skin over a bright yellow ground color, large fruit of good flavor balance of sugar and acid, and exceptional fiminess due to its non-melting flesh. The present botanical description is that of the variety as grown on 4-year-old trees grown on 'Flordaguard' rootstock under the ecological conditions prevailing at Gainesville, Fla. Variations of the usual magnitude and characteristics incident to changes in climatic growing conditions, soils, fertilization, pruning, irrigation, and pest control are to be expected. Colors (except those in common terms) are described from "The Pantone Book of Color" published by H. N. Abrams, Inc., N.Y. 1990.

Tree:

*Ploidy.*—Diploid.

*Size.*—Trees are large when trained to an open vase form.

*Vigor.*—Vigorous, and must be summer and winter pruned to keep tree height restricted and to keep center of vase open. Trees respond typically to irrigation and fertilization. Tree growth of 5 to 7 feet in height and 4 to 6 feet in width occurs in the first growing season in the field. Annual growth on mature trees averages 2 to 4 feet in length.

*Density.*—Medium to dense in branching habit and requires pruning to open the tree center which permits high sunlight entrance for enhancing fruit color and sugar.

*Form.*—Semi-spreading when pruned to vase shape. Slightly less spreading than 'UFGold'.

*Hardiness.*—Hardy with respect to typical north central Florida winters. Chill units for endodormancy are estimated at 200 cu.

*Productivity.*—Annual and regular without alternate bearing and must be fruit thinned to avoid limb breakage and obtain large fruit size. Trees annually set several times the number of fruit for a desired crop load.

Trunk:

*Size.*—Large trunk diameter attaining 16 cm diameter at a height of 30 cm at the end of 4 years growth.

*Bark texture.*—Medium smooth, but changes to medium rough as tree ages.

*Bark color.*—Variable with older bark considered mostly gray, Lead Gray (Pantone 17-1118).

*Lenticels.*—Numerous 38 per 4 square inches of surface area of trunk), small (2–4 mm length), perpendicular to the trunk with the center being Mineral Yellow (Pantone 15-1046).

Branches:

*Size.*—Strong growth of scaffold branches. This is not distinctive of the variety.

*Texture.*—Relatively smooth, medium amount of lenticels attaining size found on trunk and old scaffolds. Roughness increases with age.

*Color.*—New wood is light green, Tarragon (Pantone 15-0326) on the underside with anthocyanin on the sunny upper surface, Carnelian, Pantone (16-1435); Two-year-old wood is more brown, Cedar Wood (Pantone 17-1525).

*Crotch angles.*—Angles selected at 45 to 70 degrees in first year of tree training. Natural angles are within the normal range of standard varieties for a semi-spreading tree.

Leaves:

*Size.*—Medium; 16 to 17 cm length, including the petiole; 3.5 to 4 cm width. Measurements were made on full size leaves of vigorous upright shoots in summer growth.

*Thickness.*—Regular and average for many peach varieties. Not distinctive of the variety.

*Form.*—Lanceolate.

*Apex.*—Acuminate.

*Margin.*—Serrulate, slightly undulate.

*Base.*—Cuneate.

*Surface.*—Upper, glabrous; Lower, medium large veins that are pinnately netted.

*Color.*—Lower surface is green, Grasshopper (Pantone 18-0332); Upper surface is slightly darker green, Black Forest (Pantone 19-0315). Veins on lower surface of old leaves and into the petiole shows moderate anthocyanin development in midsummer to autumn as is typical of an 85 day fruit development period peach variety.

*Glands.*—Two to four globose glands mostly on lower leafblade, but occasionally on petiole. Leaf glands are average size for many peach varieties and are not distinctive for the variety. Leaf glands on young leaves are yellowish green, Chinese Yellow (Pantone 15-0948) in mid summer.

*Petiole.*—About 10 mm (10 to 11 mm) length; 2.5 mm diameter. Yellowish green, Golden Green (Pantone 15-0636) on young full size leaves in mid summer. Two longitudinal grooves occur on the adaxial (ventral) side.

*Stipules.*—Medium in length (5 to 8 mm), 2 per node, and abscising (deciduous) just before leaf obtains full size on summer growth, both common to most peach varieties.

*Arrangement.*—Alternate.

Flower buds:

*Hardiness.*—Hardy with respect to north central Florida winters. No damage observed following a minimum of 16F.

*Abundance.*—Moderately high, most buds set fruit in absence of spring frosts.

*Size.*—Medium, average 3.5 mm length in late autumn.

*Form.*—Plump, conic and free.

*Surface.*—Pubescent scales.

*Color.*—Brown, Bitter Chocolate (Pantone 19-1317) in late summer.

Flowers:

*Blossom period.*—With 'UFGold' peach — average February 5–7 at Gainesville, occurring over a 7 to 10 day period, dependant on ambient temperatures.

*Aroma.*—Fragrance is slight to none.

*Type.*—Showy, location and seasonally variable size, but within the range of commercial varieties. Average flower diameter 32 mm. Average petal length 16 mm; width, 11 mm. Petals are obovate and edges vary from smooth to slightly undulate.

*Color.*—Petals are Orchid Pink (Pantone 13-2010) upon opening, fading at the outer edges, but darkening in center to Geranium Pink (Pantone 15-1922) before abscising, and within the range of standard varieties.

*Flower parts.*—Pistil shape and color are withing the range of standard commercial varieties. Pistils are usually 1 per flower and pubescent. Pistils length (from tip of stigma to base of the ovary) is 12 mm and color is pale green, (Pantone 12-0626). There are 5 sepals and 5 petals. Sepals are pubescent and petals glabrous. Flower pedicel is 2 to 3 mm length, not distinguishing for the variety.

*Stamens.*—Number varies from 28 to 41. Length is 9 to 12 mm.

*Anthers.*—Light red to yellow, Orange (Pantone 16-1253) at flower opening, fading to Banana (Pantone 13-0947) before shedding, regular size.

*Pollen.*—Abundant and yellow, Pastel Yellow (Pantone 11-0616).

*Calyx cup.*—Medium (5 mm diameter and 6 mm depth) as compared to commercial varieties.

*Fertility.*—Self fertile and no cross pollination is required.

Fruit:

*Maturity when described.*—Tree ripe, May 1, 2002 at Gainesville.

*Date of first picking.*—Apr. 29, 2002 at Gainesville.

*Date of last picking.*—May 8, 2002 at Gainesville.

*Size.*—Uniform, medium large (large size for early season maturity at 100 to 120 g). Varies with number of fruit per tree, soil type, climatic conditions and cultural practices. Average equatorial diameter — 2¼ inches (57 mm). Average polar length (stem to distal end) — 2½ inches (63 mm).

*Pedicel.*—Length is 7 to 9 mm; Width is 3 to 4 mm. Color is bright green, Willow Green (Pantone 15-0525). Pedicel is enlarged at point of fruit attachment.

*Longitudinal section form.*—Round.

*Transverse section through diameter.*—Round.

*Suture.*—Inconspicuous in form and color.

*Ventral surface.*—Usually rounded.

*Base.*—Slightly retuse.

*Apex.*—Usually rounded to slight obtuse.

*Crater at pedicel attachment.*—Flaring circular, but elongated in the suture plane. Stem depressing on base of fruit. Depth is 10 mm; Breadth is 22 mm at top and 3 to 4 mm at pedicel attachment.

Skin:

*Thickness.*—Medium in comparison to commercial peach varieties.

*Texture.*—Medium in comparison to commercial peach varieties.

*Tenacity.*—Tenacious to flesh.

*Color.*—Bright red, Fire Cracker (Pantone 16-1452) with darker red stripes, Maroon (Pantone 18-1619) over 90 to 100% of skin surface at first harvest. Ground color deep yellow, Radiant Yellow (Pantone 15-1058). Fruit exposed to sunlight have a higher degree of enhanced red skin.

*Tendency to crack.*—None observed.

*Taste.*—No astringency observed.

*Pubescence.*—Short and medium soft.

Flesh:

*Ripens.*—Evenly within each fruit.

*Texture.*—Firm, fine, juicy, and non-melting when fully ripe.

*Fibers.*—Very fine, small, tender and abundant throughout the flesh.

*Aroma.*—Moderate and in the middle range of commercial peach varieties.

*Eating quality.*—Good, sweet, slightly acid. Fruit averaged 11 brix when described. Titratable acidity was 0.80 as % malic acid and penetrometer firmness was 1.4 kg as measured with a standard 8 mm tip at harvest.

*Juice.*—Abundant.

*Color.*—Deep yellow, Saffron (Pantone 14-1064) with some speckles of red, Sugar Coral (Pantone 16-16-40) throughout the flesh, especially on stressed trees under dry, hot conditions. There is no red at the pit.

*Browning by oxidation.*—Slight on tree ripe fruit beginning to soften.

*Amygdalin.*—Undetected.

Stone:

*Type.*—Clingstone, adhering to flesh even at softening.

*Size.*—Medium small; average length is 27 mm, average width at the equator perpendicular (dorsal to ventral side) to the suture is 20 mm, average width at the equator across (facing) the suture is 17 mm. Average pit wall thickness at the equator perpendicular to the suture is 4 to 5 mm.

*Color.*—Grey Sand (Pantone 13-1010) when freshly exposed.

*Form.*—Elliptic shape with an acute base and acuminate apex.

*Sides.*—Near equal.

*Surface.*—Irregularly furrowed toward the ventral edge from apex to base. Pitted from the center toward the base and apex.

*Ridges.*—Almost nonexistent, even on the suture side.

*Tendency to split.*—None observed.

*Kernel.*—Oval shape, bitter (amygdalin is abundant) and viable, but low germination without embryo culture. Average width, 8 mm; Average length 14 mm. Color light brown, Gold Earth (Pantone 15-1234) on mature fruit when first removed from stone of freshly harvest fruit.

Use: Fresh; dessert.

Keeping quality: Excellent after 2 weeks at 35F, indicating that the degree of firmness at harvest and retained in refiigeration should be highly acceptable for shipping and shelflife. Thus, tree ripe flavor should be available to the consumer.

Resistance to disease: High resistance to bacterial spot incited by *Xanthomonas campestris* pv. *pruni.* Resistance to other fruit and tree diseases are within the range for commercial peach cultivars in Florida. No unusual resistance or susceptibility to insects and diseases noted.

We claim:

1. A new and distinct peach tree variety as illustrated and described, characterized by a mid-chilling requirement, and bearing early mid-season fruit having firm, yellow and non-melting flesh of high eating quality, and an attractive, near full red skin on fruit ripening in early May with 'UFGold' at Gainesville, Fla.

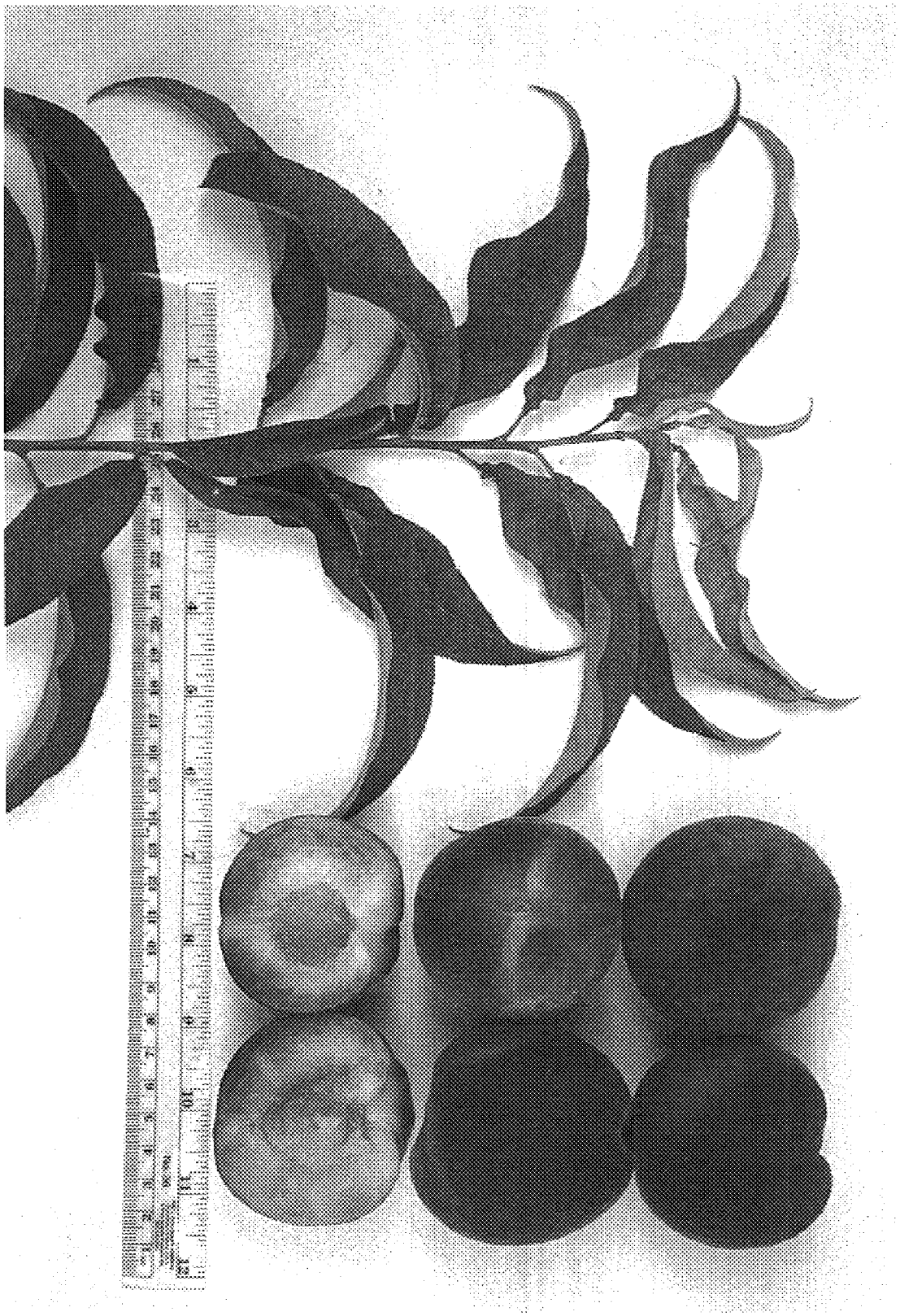

* * * * *